(12) United States Patent
Orton

(10) Patent No.: US 6,920,884 B2
(45) Date of Patent: *Jul. 26, 2005

(54) METHOD OF PROVIDING COSMETIC/MEDICAL THERAPY

(76) Inventor: Kevin Orton, 940 Calle Negocio #140, San Clemente, CA (US) 92673

( * ) Notice: Subject to any disclaimer, the term of this patent is extended or adjusted under 35 U.S.C. 154(b) by 179 days.

This patent is subject to a terminal disclaimer.

(21) Appl. No.: 10/307,248

(22) Filed: Nov. 27, 2002

(65) Prior Publication Data

US 2003/0163163 A1 Aug. 28, 2003

Related U.S. Application Data

(63) Continuation-in-part of application No. 10/211,654, filed on Aug. 2, 2002, now abandoned, and a continuation-in-part of application No. 10/207,651, filed on Jul. 26, 2002, now abandoned, which is a continuation of application No. 10/032,323, filed on Oct. 24, 2001, now abandoned, which is a continuation of application No. 09/919,493, filed on Jul. 31, 2001, now abandoned, which is a continuation of application No. 09/670,734, filed on Sep. 27, 2000, now abandoned, which is a continuation of application No. 09/289,409, filed on Apr. 9, 1999, now Pat. No. 6,488,032, which is a continuation of application No. 09/259,120, filed on Feb. 26, 1999, now Pat. No. 6,181,962, which is a continuation of application No. 08/865,253, filed on May 29, 1997, now Pat. No. 5,885,241.

(51) Int. Cl.[7] .............................................. A61K 35/00
(52) U.S. Cl. ...................................... 128/898; 604/20
(58) Field of Search ........................... 128/898; 604/20, 604/21; 607/3, 120, 134, 50

(56) References Cited

U.S. PATENT DOCUMENTS

| | | |
|---|---|---|
| 397,474 A | 2/1889 | Stanley |
| 408,607 A | 8/1889 | Flint |
| 882,378 A | 3/1908 | Friendlich |
| 1,108,686 A | 8/1914 | Bonis |
| 3,163,166 A | 12/1964 | Brant et al. |

(Continued)

FOREIGN PATENT DOCUMENTS

| | | |
|---|---|---|
| EP | 0 377 057 | 7/1990 |
| FR | 2 621 827 | 4/1989 |
| GB | 1 603 034 | 3/1978 |
| GB | 2 078 514 | 10/1980 |
| GB | 2 276 544 | 3/1994 |
| GB | 2 276 544 A | 10/1994 |
| WO | WO 87/02705 A1 | 5/1987 |
| WO | WO 90/01957 | 3/1990 |
| WO | WO 96/06656 A1 | 3/1996 |
| WO | WO 96/06656 | 7/1996 |
| WO | WO 98/53876 A1 | 12/1998 |
| WO | WO 99/62481 | 12/1999 |
| WO | WO 00/49586 A1 | 8/2000 |
| WO | WO 00/61221 A1 | 10/2000 |
| WO | WO 01/21132 A1 | 3/2001 |
| WO | WO 02/03340 A1 | 1/2002 |

OTHER PUBLICATIONS

Web Page—www.angelfire.com/biz/Korean WaterIonizer/index.html Korean Water Ionizer: 2 pgs.

(Continued)

*Primary Examiner*—Jeffrey R. Jastrzab
(74) *Attorney, Agent, or Firm*—Orrick, Herrington & Sutcliffe LLP

(57) ABSTRACT

A method for providing medical therapy treatment includes steps for preparing an electrically activated substance, and for using and applying the electrically activated substance internally to a human or animal subject. The electrical activation process of the substance includes making changes in a physical property thereof, as demonstrated by the results.

26 Claims, 7 Drawing Sheets

U.S. PATENT DOCUMENTS

| | | | |
|---|---|---|---|
| 3,794,022 A | 2/1974 | Nawracaj | |
| 4,147,775 A | 4/1979 | Schwartz et al. | |
| 4,180,079 A | 12/1979 | Wing | |
| 4,407,282 A | 10/1983 | Swartz | |
| 4,446,870 A | 5/1984 | Wing | |
| 4,474,748 A | 10/1984 | Sipos | |
| 4,487,282 A | 12/1984 | Wakatsuki et al. | |
| 4,540,403 A | 9/1985 | Theeuwes | |
| 4,572,194 A | 2/1986 | Head | |
| 4,602,909 A | 7/1986 | Csilik et al. | |
| 4,822,339 A | 4/1989 | Tran | |
| 4,926,881 A | 5/1990 | Ichinomiya et al. | |
| 4,942,884 A | 7/1990 | Ichinomiya et al. | |
| 4,944,302 A | 7/1990 | Hernandez et al. | |
| 4,980,038 A | 12/1990 | Watanabe et al. | |
| 5,012,816 A | 5/1991 | Lederere | |
| 5,058,605 A | 10/1991 | Slovak | |
| 5,188,738 A | 2/1993 | Kaali et al. | |
| 5,304,289 A | 4/1994 | Hayakawa | |
| 5,350,415 A | 9/1994 | Cywinski | |
| 5,603,915 A | 2/1997 | Nelson et al. | |
| 5,885,241 A | 3/1999 | Orton | |
| 6,139,829 A | 10/2000 | Estrin | |
| 6,181,962 B1 * | 1/2001 | Orton | 604/20 |
| 6,283,322 B1 | 9/2001 | Liff et al. | |
| 6,488,032 B1 * | 12/2002 | Orton | 128/898 |

OTHER PUBLICATIONS

Web page—www.alternativemedicine.com/digest/issue09/i09–a25.shtml"Rejuvenation Keys" 2 pgs.

Email Advertisment—Introducing: Microwater Series On, Present by High Tech H20 5 pgs.

Email Advertisment—"THM Microwater The Microwater Unit" 2 pgs.

* cited by examiner

METHOD OF PROVIDING COSMETIC/MEDICAL THERAPY

This application is a Continuation-in-part of application Ser. No. 10/211,654, filed Aug. 2, 2002, now abandoned which is a Continuation of application Ser. No. 09/919,493, filed Jul. 31, 2001, now abandoned which is a Continuation of application Ser. No. 09/289,409, filed Apr. 9, 1999, now U.S. Pat. No. 6,487,032 which applications are hereby incorporated by reference in their entirety. This application also is a continuation-in-part of application Ser. No. 10/207,651, filed Jul. 26, 2002, now abandoned which is a Continuation of application Ser. No. 10/032,323, filed Oct. 24, 2001, now abandoned which is a Continuation of application Ser. No. 09/670,734, filed Sep. 27, 2000, now abandoned which is a Continuation of application Ser. No. 09/259,120 filed Feb. 26, 1999, which issued as U.S. Pat. No. 6,181,962 on Jan. 30, 2001, which is a Continuation of application Ser. No. 08/865,253, filed May. 29, 1997, which issued as U.S. Pat. No. 5,885,241 on Mar. 23, 1999, which applications are hereby incorporated by reference in their entirety.

FIELD OF THE INVENTION

The present invention relates generally to providing cosmetic/medical therapy and more particularly to a method of preparing and using an electrically activated substance obtaining advantagous qualities for use in such therapy.

BACKGROUND OF THE INVENTION

The use of transcutaneous electrotherapy to treat medicinal conditions is known. Transcutaneous electrotherapy involves the passage of an electrical current from one electrode to another, such that the therapeutic current is caused to pass through a target tissue of the patient. Some exemplary devices used in the performance of transcutaneous electrotherapy are provided in U.S. Pat. Nos. 397,474; 3,794,022; 4,180,079; 4,446,870; 5,058,605; in French Patent 2621-827-A; and European Patent Application EP-377-057-A.

Although the use of transcutaneous electrotherapy has been around for a while, in many ways there are undesirable aspects. For example, transcutaneous electrotherapy causes electrical current to pass through the target tissue of the patient. Many patients may find this unsettling, painful or otherwise undesirable. Additionally, too much current, usually over about 1 milli-amp, can also become uncomfortable, painful, and harmful to the patient. Current also tends to concentrate near the electrodes or along current paths, which is often not desirable when trying to control the current density in tissue. In addition, the highly variable impedance nature of tissue makes it difficult to try to determine and repeat the proper treatment duration and settings.

In view of the foregoing, it is desirable to provide an effective alternative to transcutaneous electrotherapy techniques wherein electric current is not required to flow through the tissue of the patient, which is also easier and simple to apply, can more evenly distribute it's benefits, provide more accurate results, and is more effective.

Other existing medical procedures, including such procedures as surgical cut and lift, laser resurfacing, and chemical peels damage the outer layers of skin, which must then be renewed. This takes time, and there is risk of burning and scaring. Angioplasty for treatment of coronary circulation impairments is expensive, localized, and requires surgical techniques. Also, this procedure is expensive, requires skilled professional administration, and carries a certain degree of risk, as well as inconvenience, and generally requires a healing period.

Various existing inhalants are available for relief of symptoms of pulmonary conditions, but they often do not correct them, as so consequently require continual usage.

Other existing medical drug therapy techniques have limitations which may be undesirable. Drugs work by altering, interfering with, supplementing or reacting in chemical means in the body. As such, they may exhibit potent results, but will generally require a variety of different compounds to provide a useful range of therapies. There may also be side effects. Thus it is desirable to provide a substance with drug like action, for use in a medicinal way, that is relatively simple to make, simple in structure, is easy to make and apply, has a wide range of uses, more permanent results, can provide more effective results than existing medications for many conditions, and does not cause electrical current to directly flow through the tissue of the recipient, whether a human or an animal. This invention provides such a means.

SUMMARY OF THE INVENTION

The present invention provides a method for preparing a substance or solution which has unique properties. Furthermore, the substance or solution is uniquely adapted for simple, effective use. The unique physical properties are particularly useful when used in the manners described, and exhibit uniquely useful results. More specifically, molecules of the substance are thought to be forced to take on a random or unformed structure through the use of disclosed electrical energy. A technique for initiating this randomizing is disclosed. The spin, valence, structure, magnetic coupling, or bonding of the atoms is likely affected. Also disclosed is a technique for allowing very high current and energy level concentrations to occur in a solution without instigating electrolysis of the solution. Also disclosed are process time parameters, and a technique for use of the solution.

The solution herein is generally termed "electrically active".

One advantageous use of the electrically activated substance herein is in the treatment of various diseases and biological conditions. The electrically activated substance per this disclosure is able to cause or trigger a molecular or chemical action. The electrically activated substance disclosed tends to exhibit catalyst type properties when injected in biological tissue. That is to say, it tends to trigger pre-existing response mechanisms in the tissue, rather than reacting with the in a direct manner in the way a conventional drug would.

According to one embodiment of the present invention, the electrically activated substance herein largely comprises ordinary tap water, or possibly distilled water. Although water has many unusual properties, this invention is not necessarily limited to using water as a base or component of the solution. Various other compatible substances, particularly liquids, may potentially be used for an activation solution. This might include various classes of alchohols or other chemicals.

Additional materials may be included or added to the substance. In particular, placental, amniotic, serum, and stem cell types of structures may be added, either before, during, or especially after the application of the electrical signal. However, the addition of these or any biological or living or post-living cells are not an important or essential requirement for the practice of this invention. Also vitamins, analgesics, and other additives may be used.

In addition, other materials may be used or added to the water or substance without departing from the spirit and scope of the invention. For example, a thickening agent, such as PEG-150 Distearate or auramidopropyl beatine may be added to provide thickening into a paste or gel or semi-solid consistency for easier application, especially when using the substance topically.

One step of electrically activating the substance comprises applying an electrical signal to the substance. The type of signals used are important to obtaining useful results.

The use of an alternating or at least heavily pulsating direct (DC) current is an important part of the invention. An alternating current, and more particularly, a high frequency alternating current (HFAC or just AC) has been found to be a beneficial part in the process of re-structuring or randomizing the molecules or activating the solution. This is enhanced by the flow of electrons in both directions through the solution.

For example, on the + portion of the waveform, one electrode is positive (+) and one electrode is negative (−). Current will flow through the solution and, if electrically activating water, hydrogen gas will evolve at one electrode, with oxygen at the other. By reversing the polarity of the current flow (using an AC waveform) on a periodic basis, the current flow will be reversed, and the gasses evolved at each electrode will also reverse. A direct current (DC) signal current does not initiate the activation process.

In fact, a DC component in the signal will cause electrolysis to occur, which is not a desired feature of this invention. This invention does not rely on conventional electrolysis of the solution to create its activation qualities. With a DC component in the signal, there would be rapid production of hydrogen and oxygen gas, and the substance will vaporize away in a matter of minutes, − before sufficient activation occurs. There will also be undesired changes in the PH level of the solution, which is not necessary when practicing this invention.

When practicing the invention optimally, the PH balance of the medium will not change substantially during the activation process. This may be observed with a hand-held type digital PH meter. A typical reading is 7.2 at the start of the activation cycle, and a value of 7.1–7.3 at the end. (The electrical energy should be removed when making a measurement.) Of course, if the PH level should shift, as would occur with a non-symmetrical AC waveform, the shift does not necessarily mean that the solution can not be used.

The method of generating the electrical signals is known and consists generally of a power source, a signal generator and a high power amplifier.

Biological currents (electron transport functions) operate at very small currents in mammals, on the order of nano-amps and less, and so are easily overloaded at currents as small as about 1 milliamp. This limits the amount of excitation energy that is useable with existing transcutaneous devices. However, if a large amount of power is used on a bio-compatible material, new beneficial properties are obtained.

In order to overcome the power limitation, a medium, functioning as an intermediate transfer solution, —is employed. Electrical signals are applied to the medium, which is then applied to the patient after removal of current therethrough. In this way more power may be used than would normally be comfortable or safe for the patient if current were to flow through the patient.

In order to excite the solution adequately enough to become activated, it is necessary to use a relatively large amount of power. The minimum power density required is about 10 milliwatts per milliliter. Thus, if a 100 milliliter (about 4 oz.) batch is prepared, at least 1 watt and preferably 100 watts of power should be used.

If a simple 60 hertz AC line waveform were used, it is not possible to activate the solution. This is because at the high power levels required, the solution exhibits strong electrolysis action at low frequencies and the solution vaporizes away before the solution can become sufficiently active.

In order to allow the solution to absorb high power levels and yet prevent premature electrolysis of the solution, a specific novel technique is employed. This comprises using an electrical signal that preferably comprises an alternating current signal operating in the frequency range of between approximately 10 KHz and approximately 1 MHz, with between approximately 25 KHz and approximately 100 KHz being optimum. When operating at the specified frequency, the gassing away of the solution is reduced by about 100 to 1000 times that of a lower frequency or DC signal. There are also substantially more phase reversals of the current flow per unit of time, and orders of magnitude more current and power may be used. The electron agitation is also increased over lower frequencies.

By switching the polarity of the current on a sufficiently quick periodic basis, the atoms may be partially electrolyzed (separated), yet recombined back together again before any gas escapes. This partial electrolysis, current phase reversal, then recombining and then re-separating again may be what contribute to the substance becoming electrically activated. At this frequency, the current reverses direction faster than molecules can be atomized, broken up, and escape, and little gassing is released. The new properties that the solution takes on at the specified frequency and power levels then allow it to absorb significantly more energy than at lower frequencies. In fact, the solution can now absorb enough energy to cause electrical conduction heating of the solution. This is the ideal condition for creating the activated substance. The temperature rise of the substance during activation will be approximately at least 3, 4, or 5 degrees and up to approximately 100 degrees Fahrenheit above ambient, depending on the actual power level used.

The frequency used is critical to the success of the device. The substance will not become properly electrically activated if the correct frequency is not used. The frequency range called for is the one that allows the most biocompatible activation. For example, if a frequency of 60 hertz is used, the substance will electrolyze away in only a few minutes at the power levels called for in this invention. Additionally, the substance will just not generate the biological response that frequencies in the range specified will. At frequencies above about 1 Mhz, the present medium will not take on the biological activation qualities, although there may be other mediums which will respond at that frequency. For example, applying microwave frequency energy to water will not result in biologically active activation of the substance. Thus the frequencies specified are found to work best.

It is thought the current and frequency range of this invention causes the molecules or atoms to become more fully dissociated and unformed. This means groups of atoms or molecules that normally gather together are broken apart into the smallest possible units. They may also take on a random spin, where electrons are not shared between atoms of a molecule in a familiar and stabilized manner. The bonding levels may also be affected. When partially separated molecules are reformed, the atomic structure may take on slightly different formations in the presence of the applied power. It is thought this random state reforming is what makes the substance active.

Preferably, the alternating current has approximately minimal direct current bias to prevent PH shift and gassing. In order to mitigate direct current bias, the electrical signal is preferably applied to the substance via a capacitor-resistor network. Alternatively, the electrical signal is applied to the substance via an isolation transformer.

The electrical signal preferably has a voltage of between approximately 50 volts rms and approximately 150 volts rms.

The electrical signal is applied to the substance to be electrically activated via at least one pair of electrodes. A plurality of pairs of electrodes may be utilized, if desired. For optimum results, the electrodes are comprised of an electrically and biologically inert, non-reactive metal or a non-metallic material having a low atomic number and low resistance. For example, gold, carbon, and graphite-carbon material are suitable. It has been found that lead, aluminum, copper, and other metals are not recommended for the practice of this invention, as they can cause lead ions, for example, to leach into the solution, potentially poisoning the patient. Silver provides possible antibiotic, antiseptic properties to the substance, and may optionally be used or added to the substance when this is desirable.

Additionally, multiple pairs of electrodes may be used with various different phase relationships. In this case, it may not be necessary for there to be minimal DC bias at all, as if one pair of electrodes has a positive DC bias, and another pair has a negative DC bias, the net charge bias into the solution may be near zero, thereby effectively eliminating the undesired electrolysis effect.

When distilled water is to be electrically activated, then a substance must often be added to the water to introduce impurities therein, so as to facilitate current flow therethrough. According to one embodiment of the present invention, sodium chloride (salt) or minerals are added to form an electrolyte from distilled water.

According to the preferred embodiment of the present invention, the additive substance, e.g., sodium chloride, is added to the distilled water while monitoring current flow therethrough, until the desired current is obtained. This process makes it easier for the operator, and provides more consistent results.

According to a preferred embodiment of the present invention, approximately 1 amp rms of current is caused to flow through the substance to be electrically activated. Typically, a voltage of approximately 100 volts rms is required to effect a current of 1 amp rms. It has been found that currents as low as 1 milliamp may be used, if desired. Preferably, at least 10 milliwatts of power per milliliter of substance are utilized. When a large amount of power is used in the activation process, new beneficial properties are obtained. Those skilled in the electrical art will appreciate that the voltage required to effect the desired current is dependent upon the conductivity of the substance being electrically activated.

Topical application of the electrically activated substance of the present invention has been found to be effective in mitigating wrinkles on human skin.

Additionally, the substance may be taken orally to obtain additional benefits. When taken orally, approximately 2 ml of the electrically activated substance is preferably ingested per day for approximately 6 weeks.

Furthermore, the substance has also been found to provide useful qualities for the treatment of internal conditions if applied correctly.

These, as well as other advantages of the present invention will be more apparent from the following description and drawings.

DETAILED DESCRIPTION OF THE PREFERRED EMBODIMENT

The detailed description set forth below in connection with the appended drawings is intended as description of the presently preferred embodiment of the invention and is not intended to represent the only form in which the present invention may be constructed. The description sets forth the functions and the sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

The electrically activated substance and method for making the same of the present invention are illustrated in FIGS. 1–13 of the drawings which depict presently preferred embodiments thereof.

Figure 1:
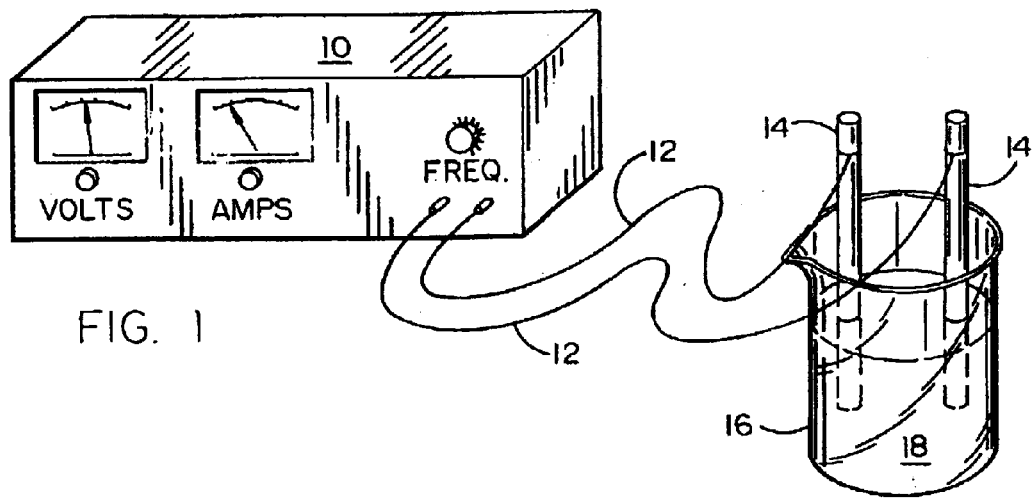
FIG. 1 shows apparatus including a variable frequency current source being utilized to electrically activate a liquid contained within a beaker.

Referring now to FIG. 1, a variable frequency current source 10 is electrically connected, via wires 12, to probes or electrodes 14 which are at least partially immersed within the substance 18 to be electrically activated, which is contained within a beaker 16. Alternatively, a fixed frequency current source may be used.

The variable frequency current source 10 preferably generates an output with a frequency within the range of from approximately 10 KHz to approximately 1 MHz, and a voltage output from approximately 50 volts rms to 150 volts rms, and having a maximum current output in excess of 1 amp rms, and provides preferably a generally symmetrical alternating current waveform.

Figure 5:
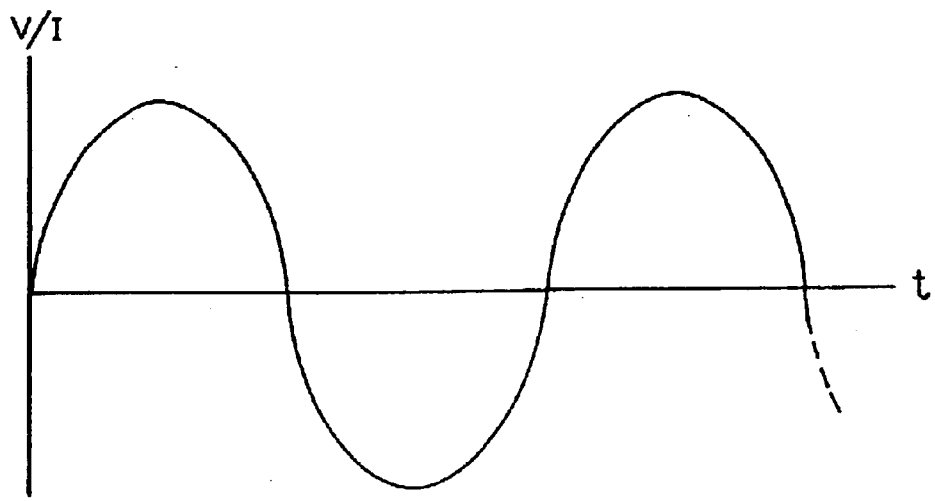
FIG. 5 illustrates one example of an alternating current waveform at the output of the current source of FIG. 1.
Figure 13:
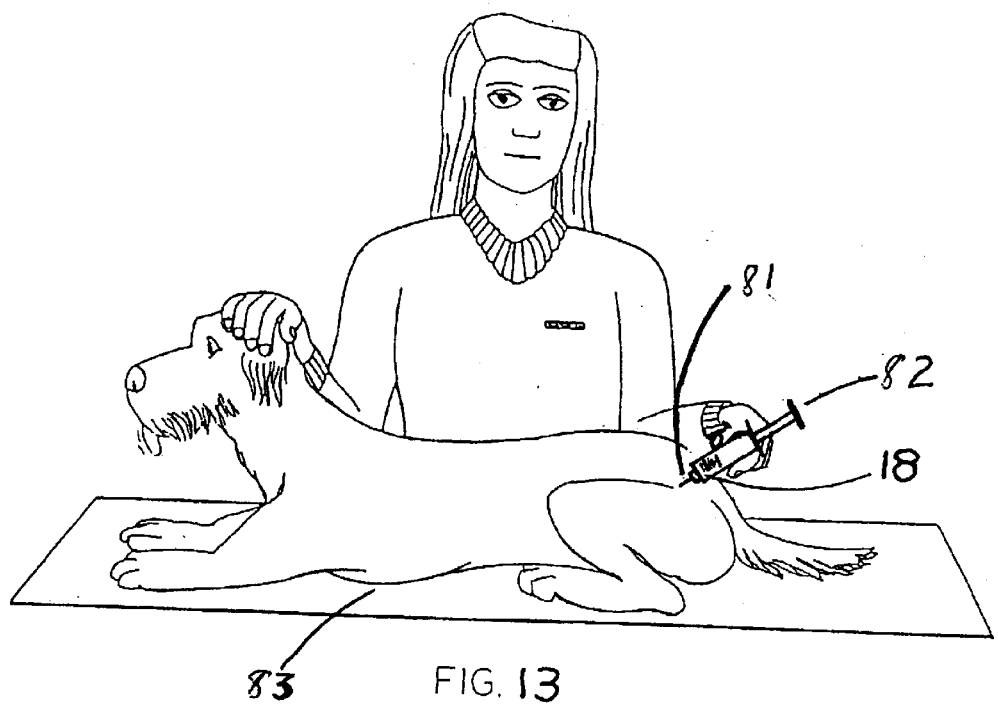
FIGS. 6–8 and 13 illustrate the electrically activated substance being applied to biological tissue.

According to the preferred embodiment of the present invention, the variable frequency current source 10 also provides an alternating current output having minimal direct current bias, as illustrated in FIG. 5 of the drawings.

In order to re-structure the molecules in the solution within the beaker 16, a high frequency alternating current (AC) signal, preferably having a generally symmetric waveform, is utilized. Thus, for example, referring to FIG. 5, a sinusoidal waveform is suitable, as would be a square AC waveform, a triangular AC waveform, or any odd-shaped AC waveform with preferably equal energy in each polarity. A square wave generally provides the highest power and best result. Those skilled in the electrical art will appreciate that various other waveforms, both symmetrical and non-symmetrical, would likewise provide alternating flow of current. Additionally, various other combinations of waveforms may likewise be suitable if they provide a beat or resonance or modulation signal within the 10 Khz to 1 Mhz band.

According to the preferred embodiment of the present invention, the frequency output of the variable frequency current source 10 is capable of being swept or automatically varied between a minimum and maximum frequency. Alternatively, the variable frequency current source 10 is capable of being manually swept in frequency.

The wires 12 preferably comprise copper wires having a current rating sufficient to carry the required current, e.g., 1 amp rms, without excessive heating.

Typical dimensions for the electrodes 14 are 3 mm thick, 20 mm wide, and 10 cm long. However, as those skilled in the art will appreciate, various different dimensions and cross-sectional configurations, e.g., round, oval, square, triangular, etc., may likewise be suitable.

Preferably, the electrical resistance of the finished electrodes is less than 500 ohms/cm$^2$, preferably less than 50 ohms/cm$^2$.

Further, according to the preferred embodiment of the present invention, the two electrodes are positioned several centimeters apart in a 250 ml container, e.g., the beaker 16. The beaker 16 is preferably formed of a non-conductive material, such as glass or plastic. Thus, as described herein, the method for electrically activating the substance 18 is preferably practiced utilizing approximately 200 ml of the substance at a time. The actual quantity of substance electrically activated may be varied widely by varying the dimensions of the container, electrodes, and by varying the strength of the electrical signal appropriately.

In one embodiment, current flow through the substance 18 being electrically activated is monitored as an electrolytic substance is added thereto so as to form an electrolyte. For example, when water is being electrically activated, then sodium chloride is added to the water, so as to form an electrolyte. As the sodium chloride is added to the water, current flow through the water may be monitored until the desired current flow is achieved, thereby indicating that sufficient sodium chloride has been added to the water.

According to the preferred embodiment of the present invention, approximately 1 amp rms of current is caused to flow through the substance 18 being electrically activated while a voltage of approximately 100 volts rms is applied thereto. Various other voltage and amperage levels are likewise suitable.

Typically, current is allowed to flow through the substance being electrically activated for approximately 4–8 hours. At this point there will usually be small gas bubbles formed upon the electrodes. At this point, the substance has been fully electrically activated and is ready to use.

Figure 4:
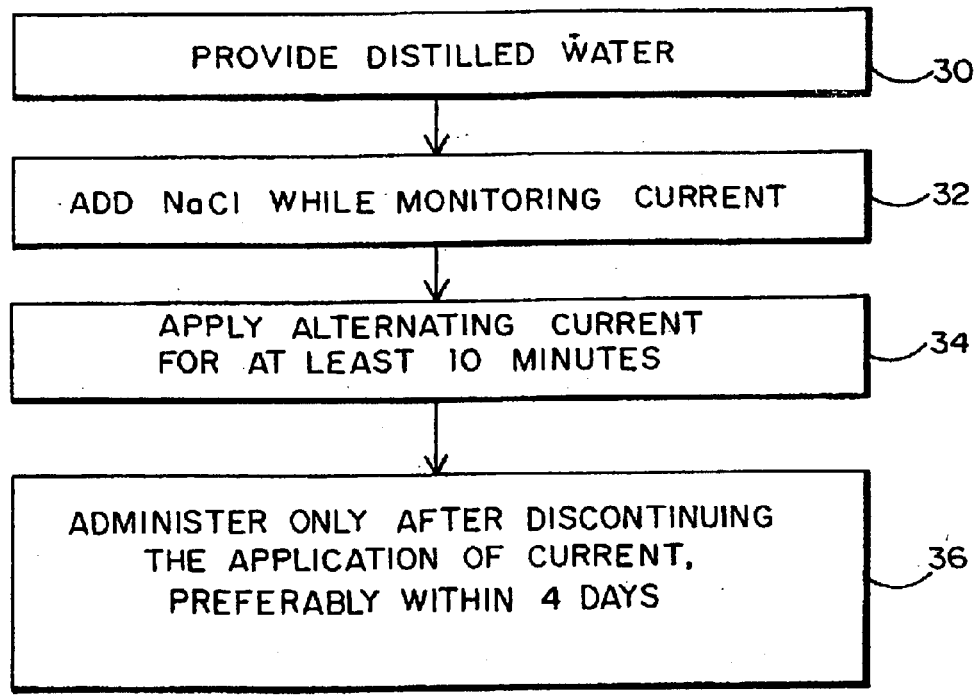
FIG. 4 is a flow chart showing the steps involved in the practice of the therapy method, according to the present invention.

The degree to which the substance 18 is electrically activated, and thus the effectiveness thereof, is directly related to the voltage applied to the electrodes 14, the spacing of the electrodes, the current caused to flow between the electrodes, and, to some extent, the length of time that the current is applied. As indicated in FIG. 4, current must flow between the electrodes for a minimum of at least 10 minutes before any usable results are typically obtained. It is thought that the application of current for a time period in excess of 8 hours produces little additional effectiveness of the electrically activated substance. The recommended period of time is 4–12 hours.

The electrically activated substance is typically active for only a limited amount of time after current flow therethrough has ceased. The electrically activated substance is thought to be most effective if utilized within approximately 4 hours after its production. The electrically activated substance is thought to be somewhat effective for up to 4 days after its production, and almost totally diminished after 7 days. It is believed that the decay in the effectiveness of the electrically activated substance is logarithmic in nature, with more than half of the effectiveness thereof lost within approximately 24 hours. Thus it is important to use the substance promtly to derive the benefits described herein.

The specified values for the applied voltage, duration, and conductivity of the medium may be varied somewhat. Indeed, a reduction in the effectiveness of the electrically activated substance may be compensated for by varying one or the other of the production parameters.

For example, a lower voltage may be utilized if additional sodium chloride is added to the solution. However, if too much sodium chloride is added, then the solution may become less bio-compatible. Conversely, if less sodium chloride is utilized, then a higher voltage is necessary to obtain sufficient current flow through the substance. Inadequate current flow through the substance results in substantially reduced effectiveness of the electrically activated substance.

Figure 10:
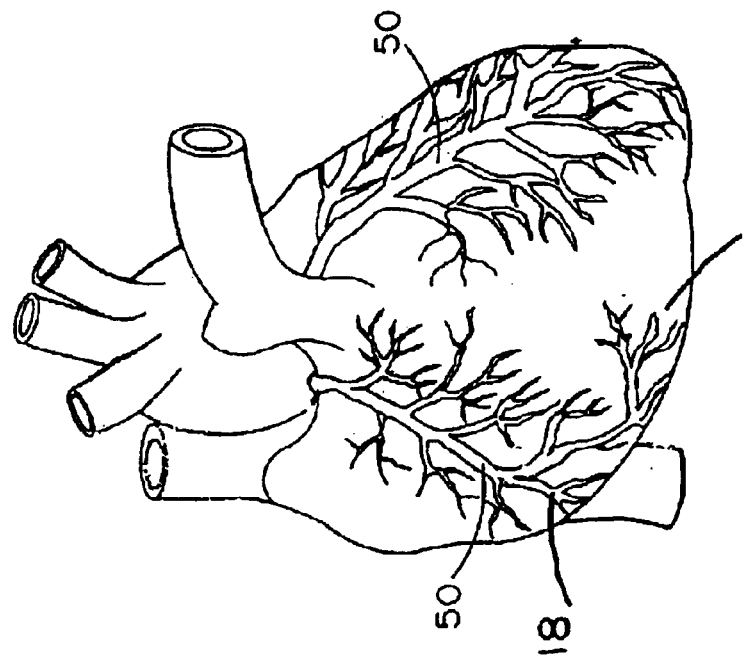
FIGS. 9, 10, 11a–c, and 12a–b show tissue changes and results obtained after the electrically activated substance has been applied thereto.
Figure 9:
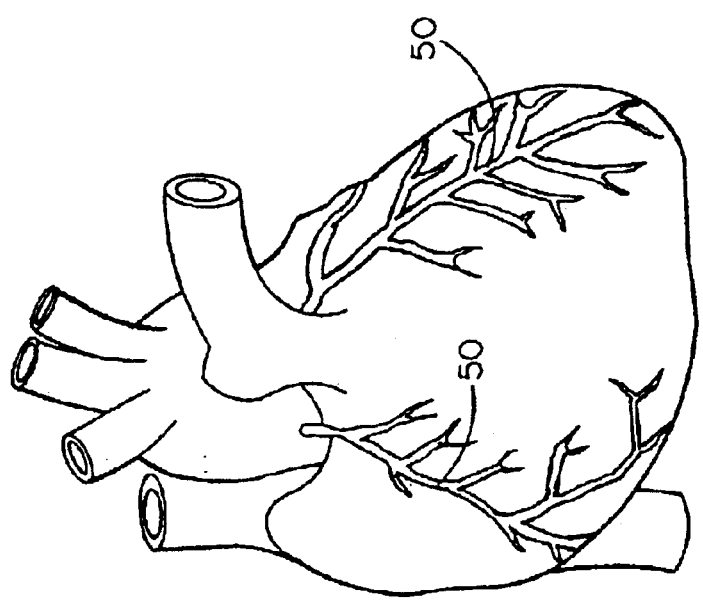
Figure 11A:
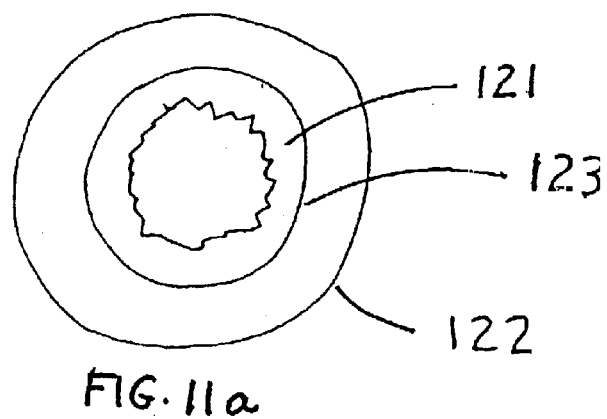
Figure 11B:
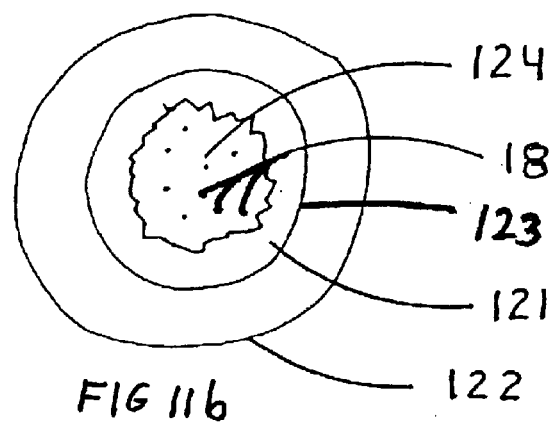
Figure 11C:
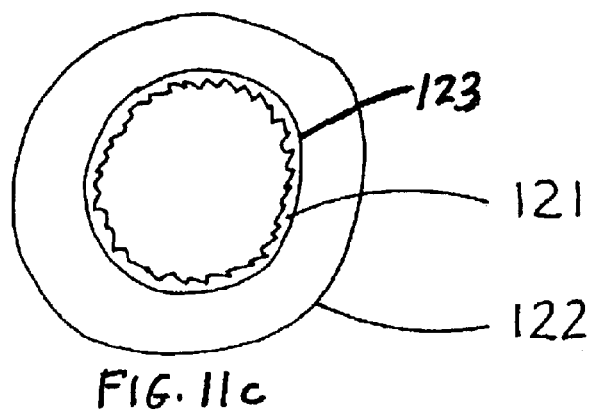
Figure 12A:
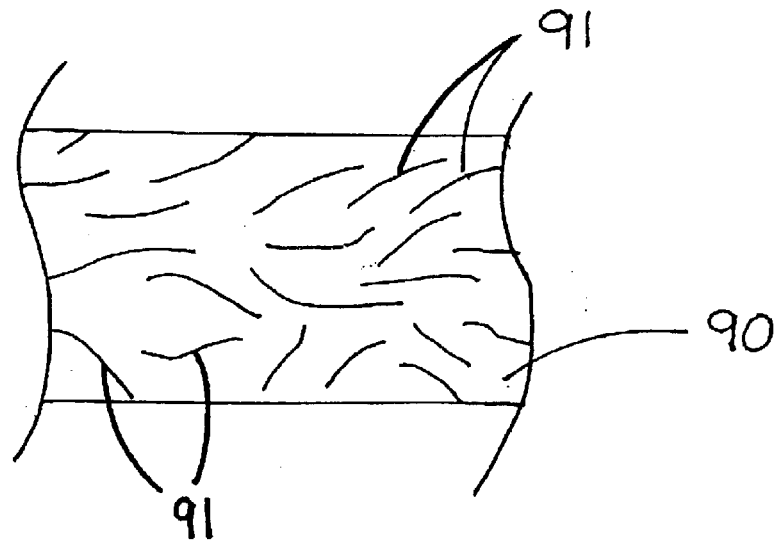
Figure 12B:
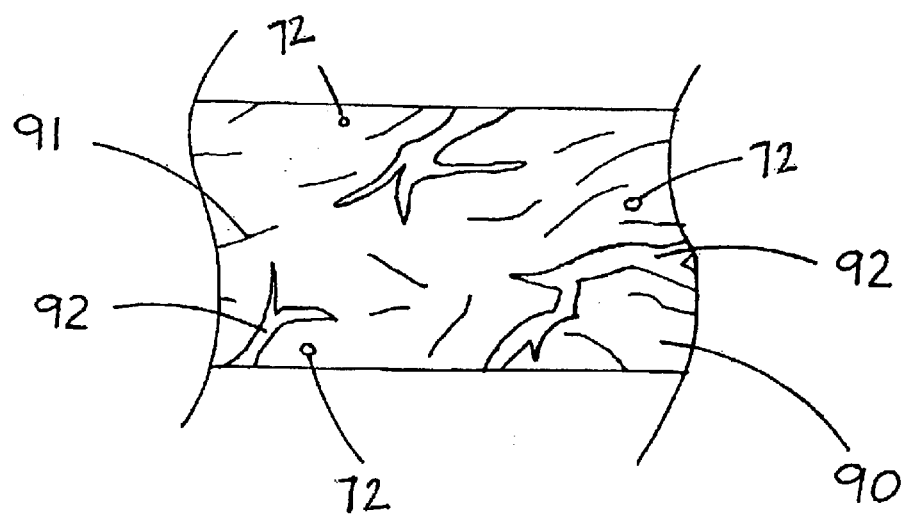

It is thought that the electrically activated substance of the present invention, when applied to biological tissue, initiates a weak electrical (or ionic) signal in the tissue, similar to the alert signal that occurs when a mechanical strain to the tissue has occurred. This is possibly caused by the spin, valence, or magnetic coupling or polarizing activity of the activated substance. The activated substance may possibly work by loosening weak molecular bonds in the tissue, thereby causing a regeneration response as the bonds or tissues recover. The activity of the substance triggers accelerated metabolic activity in the treatment area. Blood flow accelerates while cellular metabolic activity and interactions increase. As is best shown in FIGS. 9 and 10, capillaries and/or blood vessels 50 dilate following the treatment and there is increased cellular activity. Toxins, free radicals, metabolic waste and remnant material may be re-formed or flushed away.

The electrically activated substance of the present invention need not be applied to fresh injury sites. It may interfere with the timing and development of the natural current of injury, thereby inhibiting the healing process. However, once the injury has stabilized, the electrically activated substance of the present invention may be applied thereto so as to enhance or re-stimulate the healing process.

One use of the electrically activated substance of the present invention is the treatment of skin sagging. Preferably, the water is activated with a frequency of between approximately 50 KHz and 100 KHz. When injected for this purpose, there is a uniform reduction of sagging througout the body.

After each application, the recovery phase typically has a duration of approximately 1 to 7 days. After about 4 days, most of such recovery has occurred. At the end of the recovery phase, another treatment may be applied. It has been found that the recovery phase must be complete before a subsequent treatment, so as to avoid overwhelming the response mechanism.

It has been found that approximately three to six such treatment sessions are typically required for maximum results. One session every one to two weeks. The more degenerated the tissue, the more dramatic the results are. The substance also exihibits strong antiviral properties. The general result is renewed appearance, without surgery, grafting, patchwork, dermabrasion, laser vaporization, or other invasive or mechanical techniques. Additionally, electric current is never caused to pass through living tissue or cells directly.

Figure 6:
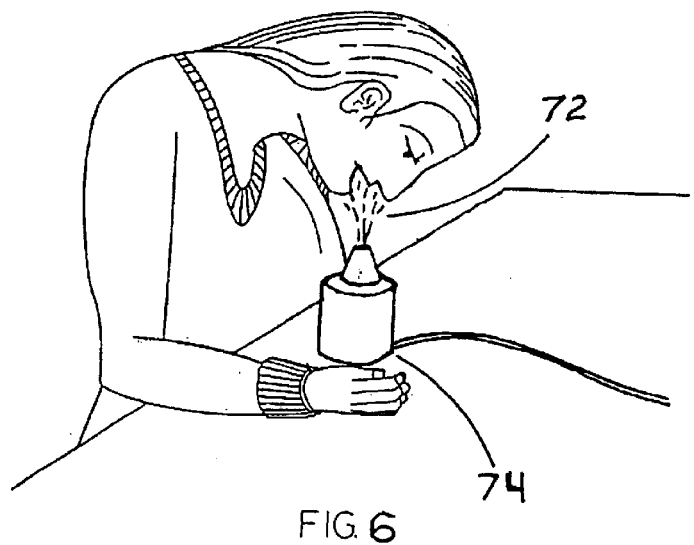
Figure 8:
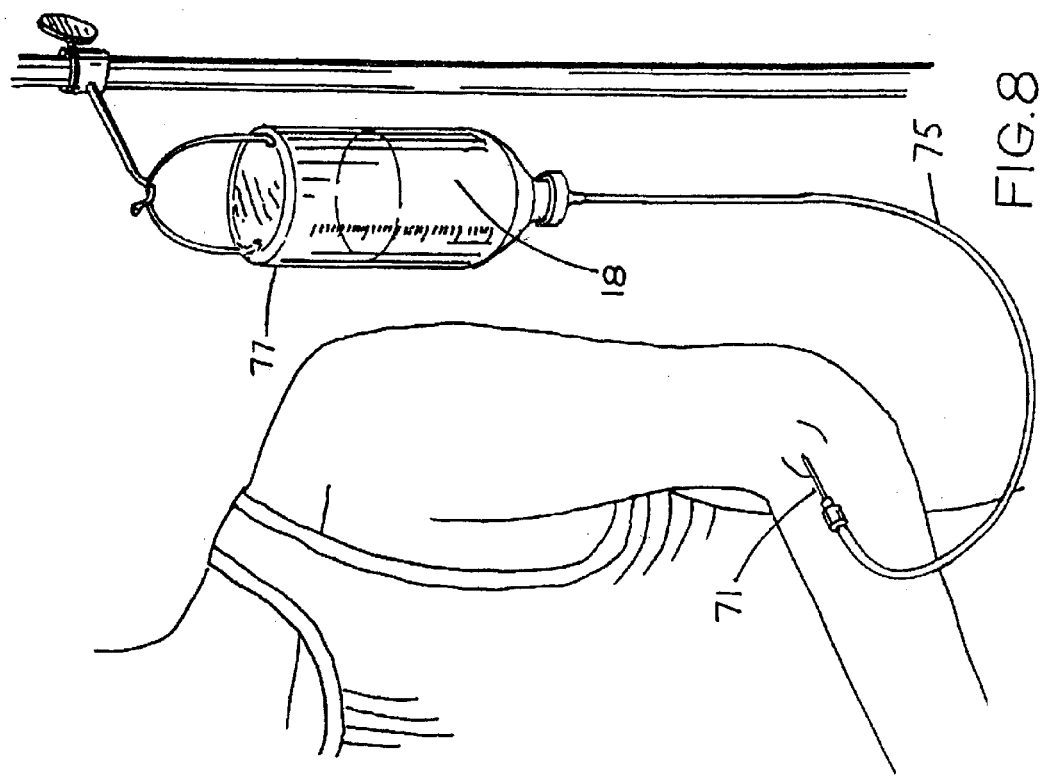
Figure 7:
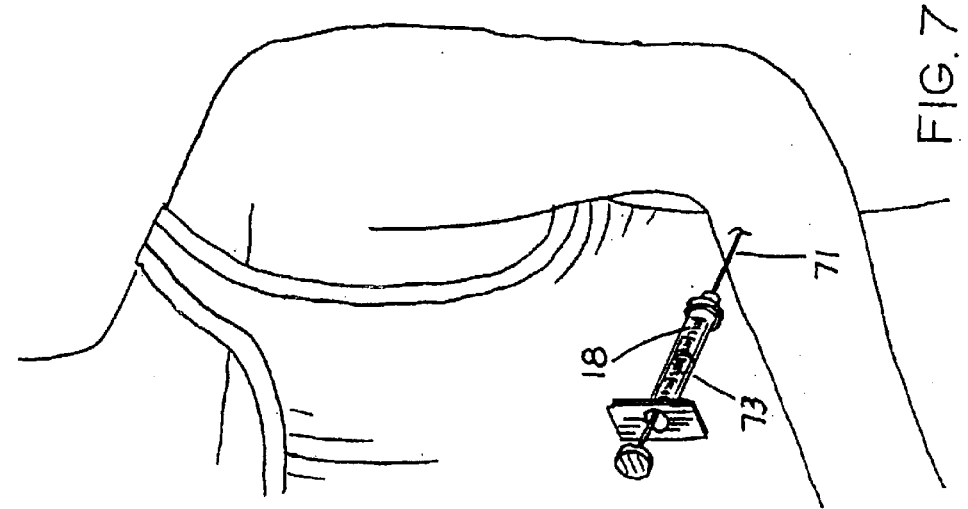

In addition to being used to treat wrinkles, the substance may also be advantageously used to treat pulmonary conditions. This is shown in FIG. 6. The electrically activated substance 18 is inhaled as a mist, or droplet form. This is preferably accomplished with the use of a conventional nebulizer 74 to convert the liquid to a vaporous material 72.

Such nebulizers are commercially available through various health care providers. Some models use compressed air or mechanical vibrations to convert a liquid or fluid to a fine mist. One such device is sold under the trademark “Micro Air” by Omron Industries. This device breaks the liquid into small particles from approximately 1 micron to 10 microns in size. These particles are clumps of molecules. When the substance is converted to a vaporous mist 72 in this manner, the electrically activated properties of the substance are found to remain. When the electrically activated substance 72 is inhaled, additional advantages and benefits to the recipient are realized. For example, when inhaled as a mist, the substance may be used to beneficially treat lung and pulmonary tract problems and disorders.

That is, pulmonary fibrosis, some types of emphysema, and other conditions may be treated in this manner. Interstitial fibrosis occurs when lung tissue becomes scarred and looses its flexibility and elasticity. This can happen after an infection, for example, or contact with an irritant and can make breathing difficult and even painful. There may also be a loss of capillary and blood-gas (air) exchange function. This condition can be improved when the vaporous mist 72 is inhaled.

FIG. 12*a* shows a cutaway patch of pulmonary fibrosis tissue 90. The tissue 90 is largely composed of fibrous strands 91. There are a lack of blood vessels, and the tissue is stiff. FIG. 12*b* shows the same portion of tissue 90 after coming into contact with the vaporous mist 72 of FIG. 6. The mist 72 helps to soften and diminish the fibrous tissue 91 and generate new blood vessels 92, thereby helping to restore normal capillary action and lung function.

Emphysema occurs when air sacs (aveoli) in the lungs burst. This is the result of weakened connective tissue. It is often initiated by air pollutants. The active-energy properties of the substance of this invention acts to improve the condition of the connective tissue and dislodge and remove contaminants. In this way further destruction is minimized and even some function restored.

Arterial plaque is another condition which is desirous to treat. This is a commonly occurring condition. It is partly influenced by diet. The plaque is largely composed of fats and lipids which have not been metabolized. These fatty deposits become attached to artery walls and surfaces and can build up over a period of time. These same fatty deposits may also build up in other tissues throughout the body. If the buildup continues, the plaque can reduce the size of arterial passageways, thereby inhibiting blood flow and impairing chemical function and activity. The fatty deposits may also accumulate in the body in general.

This is shown in FIG. 11*a*. The cross sectional view of an artery 122 has a build up 121 on the interior lining 123 which constricts its size, reducing the flow of blood therethrough.

The activated substance of the invention, when prepared as described herein, has been found to posses unique capabilities resulting in an effective and useful technique of treating such a plaque condition when the substance is injected into the blood stream. A syringe, catheter, or other such type of device may be used to effect the internal injection. This is shown in FIG. 7. A hypodermic needle 71 is attached to a syringe 73 or a container containing the electrically activated substance 18. The needle 71 is inserted through the epidermal layers of skin in order to inject the substance 18. In FIG. 8, an I.V. feed may also be used. A hypodermic needle 71 is attached to a tube 75 and a container 77 containing the electrically activated substance 18. The needle 71 is inserted through the epidermal layers of skin in order to inject the liquid 18.

FIG. 11*b* shows the artery 122 of FIG. 11*a* with the activated substance 18 contacting the blood 124 and the plaque 121. FIG. 11*c* shows the same artery 122 with the plaque 121 diminished in size after the treatment.

FIG. 13 shows a hypodermic needle 81 connected to a syringe 82 that carries the activated substance to be injected through the skin of an animal.

Graduation marks on the syringe 73 or the IV container 77 measure the amount of activated liquid 18 to be applied in a dose. When injected, the typical dose rate is one to two cc’s per 100 pounds of body weight.

When injected in this way, blood flow and metabolic activity accelerates and increases beginning about 15 minutes after the injection. There will begin a flushing action in the tissue. The heart will beat stronger. There may be a very slight fever. There is a slight tingling sensation, but no pain. This will last 1–2 days. After this period of accelerated blood flow, the body enters a recovery phase wherein the cellular structure thereof is rebuilt.

When taken internally as an injection or IV into the blood stream, the molecular action of the electrically activated substance then becomes useful to dissolve, solubolize, loosen and remove fatty deposits and plaque buildup from the artery walls. This increases capillary and general blood flow and action. When the fatty deposits which commonly occur in the blood vessels and throughout the body and blood flow system are cleaned away and solubolized as described herein, the chemical and metabolic efficiency and effectiveness of the body therafter increases greatly, causing significant and substantial improvements in the functioning, operation, and regeneration ability of most all body systems and processes. This will then allow the strengthening of arterial walls and improve the production of collagen and ligament type support structures. Thus the method provides a new, useful and effective treatment for plauqe build up conditions and positive additional benefits. The process thus also serves to provide pain relief to the recipient.

There are minimal other outward signs during treatment, however the skin may become temporarily wrinkled. The wrinkling is caused by the skin drawing together on the inside of the body, resulting in bunching up on the outside. This fades away after a while. After the first treatment, and particularly after 3–6 treatments 1 week apart, facial characteristics are smoothed and sagging features become lifted.

Other typical uses for the substance when injected are for the treatment of internal organs in general, as well as the blood and circulation system, and other textbook medical/cosmetic conditions, and is applicable to both humans and animals.

When used as an internal injection or IV, the substance is often best administered several times over a period of weeks or months. The first few treatments may be at a lower dosage rate to avoid an excessively strong reaction the first time the product is used.

Although an exemplary technique has been disclosed, there are other acceptable means of injecting the electrically activated substance into the body. It may also be applied with somewhat effectiveness as a douche or applied through the use of various tubes and with other devices without departing from the spirit and scope of the invention.

The substance may also be inhaled or injected along with other materials, nutrients, and drugs, without departing from the scope of this invention.

Because the electrically activated substance of the present invention functions as a transfer agent or medium, there is no current flow from the current source through biological tissue. Thus, there is no chance of burns, thereby enhancing the safety of such treatment. Further, there is no muscle contraction or nerve impulse firing as a result of using the electrically activated substance of the present invention, as is common during contemporary transcutaneous electrotherapy. Furthermore, there is substantially no removal of tissue, unlike dermabrasion and other techniques, and no acid/base effects on the body from PH shifts.

Although several uses have been described, there are of course many other medical conditions in both humans and animals which may respond favorably in this manner. For example, the substance has been found to have strong anti-viral properties, and may be used by itself or with other drugs, as well as for generally treating pain. The substance is also useful in treating and repairing conditions associated with damaged and cross-linked protein structures.

Figure 2:
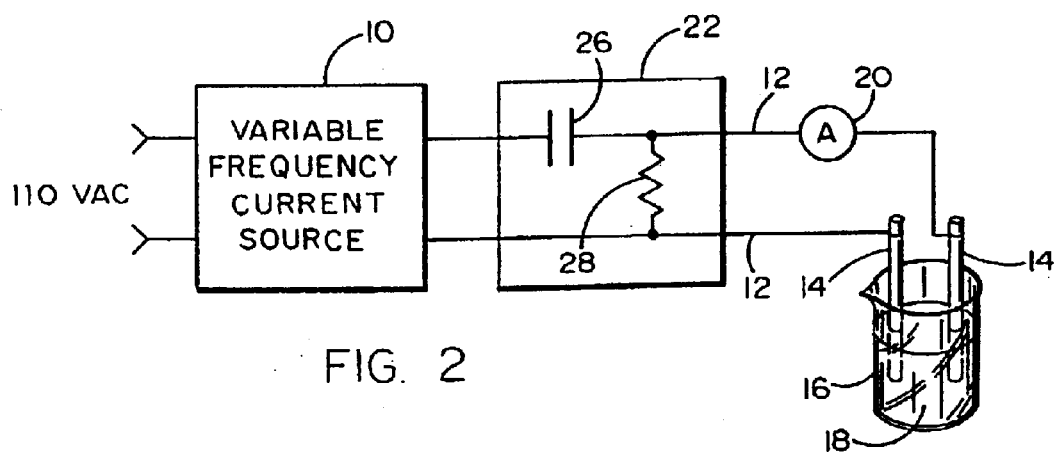
FIGS. 2 and 3 are block diagrams showing alternate configurations of the apparatus of FIG. 1.
Figure 3:
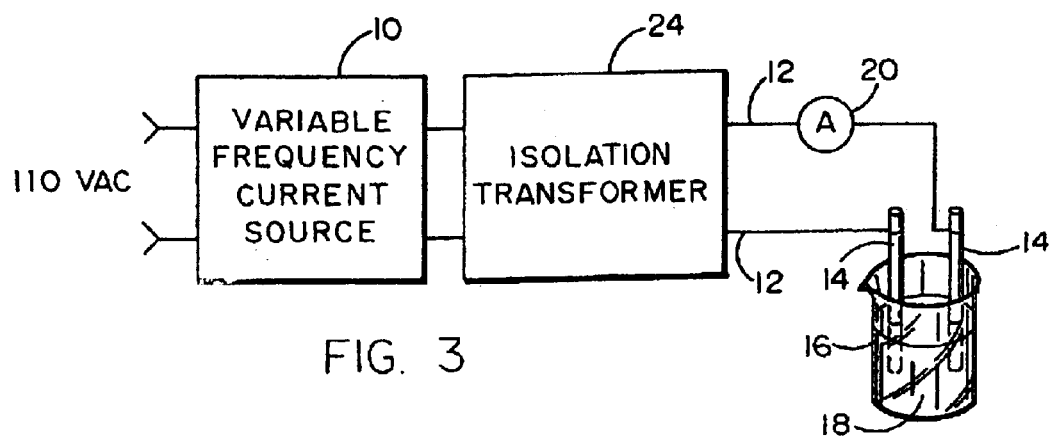

Referring now to FIGS. 2 and 3, if the variable frequency current source 10 does not provide approximately 0 direct current bias, then the output thereof can be processed so as to mitigate direct current bias.

With particular reference to FIG. 2, a resistor-capacitor network 22 may be used to filter the output of the variable frequency current source 10, so as to mitigate direct current bias. Such a resistor-capacitor network comprises at least one capacitor 26 in series with the substance 18 being electrically activated and at least one resistor 28 in parallel therewith. The resistor-capacitor network 22 functions according to known principles to mitigate the presence of DC bias in the substance being electrically charged. Those skilled in the art will appreciate that various other types of filters may be utilized. For example, a capacitor inductor network may be utilized.

With particular reference to FIG. 3, an isolation transformer 24 isolates the substance 18 to be electrically charged from direct current bias present in the output of the variable frequency current source 10.

In any instance, when the variable frequency current source 10 does not include a means for monitoring current flow through the substance 18 being electrically activated, then such means is preferably included in the electrical path of the electrodes 14. For example, an amp meter 20 may be inserted in line or applied inductively to one of the wires 12 which provide an electrical pathway for the current which travels between the electrodes 14. Alternatively, an oscilloscope may be utilized to monitor current flow and voltage between the electrodes 14.

Referring now to FIG. 4, the method for forming the electrically activated substance 18 of the present invention generally comprises the step 30 of providing distilled water, the step 32 of adding sodium chloride to the distilled water while monitoring current flow between the electrodes 14, the step 34 of applying alternating current to the electrodes 14 and the step 36 of administering the electrically activated substance, preferably within four hours after the electrical activation thereof.

The electrically activated substance is only administered after first discontinuing the application of current thereto. In this manner, the electric current can be applied to an intermediate material, (i.e., the electrically activated substance), rather than directly to a person. Thus, a substantial amount of power may be applied to the electrically activated substance, without undesirable interference with biological processes which would occur if an electrical signal of strong energy were applied directly to a recipient. Indeed, according to the preferred embodiment of the present invention, much more power, (for example 100 watts), can be applied to the electrically activated substance than could comfortably be tolerated by human tissues.

The minimum amount of power applied to the substance during electrical activation thereof must be sufficient to overcome the activation decay rate of the substance. A small activation energy will disperse as quickly as it is generating, prohibiting adequate activation of the substance. It has been found that the application of at least approximately 10 milliwatts of electrical power, and preferably 100–400 milliwatts, per milliliter of substance results in an acceptable decay rate.

Non-distilled or tap water or other bio-compatible compounds, including tissue products, may be utilized instead of distilled water. It has been found that tap water is frequently suitable for use in the practice of the present invention. However, as those skilled in the art will appreciate, the types and amounts of impurities found in tap water vary considerably from one location to another. Thus, if an accurate analysis of the tap water to be utilized is not available, then the effectiveness and current flow therethrough may be determined by trial and error.

Various other electrolyte forming substances, other than sodium chloride, are likewise suitable including but not limited to potassium, salts, and minerals.

The application of alternating current during step 34 to the substance to be electrically activated preferably takes place for a duration of approximately 4 to 8 hours. After this amount of time, there may be small gas bubbles on the electrodes.

The electrically activated substance is created using the power levels, frequencies, current densities, and dosage quantities described herein, or parameters comparable to those described herein. When the substance is produced in this manner, it takes on unique properties The electrically activated substance is created using the power levels, frequencies, current densities, and dosage quantities described herein, or parameters comparable to those described herein. When the substance is produced in this manner, it takes on unique properties (possibly on an atomic level), which make it particularly well suited for the practice of the present invention.

It is understood that the exemplary methods described herein and shown in the drawings represents only a presently preferred embodiment of the invention. Indeed, various modifications and additions may be made to such embodiment without departing from the spirit and scope of the invention. For example, various different sizes, shapes, and configurations of the container, the electrodes, and the source and type of alternating current are contemplated. Further, the use of water as the electrically activated substance is by way of example only, not by way of limitation. Indeed, it is also anticipated that gases, as well as liquids and conductive solids may be electrically activated according to the techniques of the present invention.

Thus the invention provides a new and useful therapy.

These and other modifications may be adapted to the present invention in keeping with the original spirit and scope of the invention.

What is claimed is:

1. A method for preparing a substance for use as a medicament in providing treatment to the body of a recipient, said method including the steps of:

placing an electrically conductive substance in a container such that said electrically conductive substance is separated from the body area of the recipient in need of treatment;

locating at least one pair of electrodes within the electrically conductive substance of said container and spacing said pair of electrodes from one another;

connecting an alternating current source to said at least one pair of electrodes and operating said current source to generate alternating current having a frequency lying in a range of frequencies between 10 KHz and 1 MHz so that current flows through said electrically conductive substance and between said electrodes for at least 10 minutes, and;

removing said alternating current flow through said electrically conductive substance.

2. A method for preparing a substance for use as a medicament in providing treatment to the body of a recipient, said method including the steps of:

placing an electrically conductive substance in a container such that said electrically conductive substance is separated from the body area of the recipient;

locating at least one pair of electrodes within said container of electrically conductive substance and spacing said pair of electrodes from one another;

connecting an alternating current source to said at least one pair of electrodes and operating said current source to generate an alternating current having a frequency lying in a range of frequencies between 10 KHz and 100 KHz so that current flows between said electrodes and through said electrically conductive substance for at least 10 minutes, and;

removing said alternating current flow through said electrically conductive substance.

3. A method for preparing a substance for use as a medicament in providing treatment to the body of a recipient, said method including the steps of:

placing an electrically conductive substance in a container such that said electrically conductive substance is separated from the body area of the recipient in need of treatment;

locating at least one pair of electrodes within said container of electrically conductive substance and spacing said pair of electrodes from one another;

connecting an alternating current source to said at least one pair of electrodes and operating said current source to generate an alternating current with an output power of at least approximately 10 milliwatts per milliliter of said electrically conductive substance in said container so that current flows between said electrodes and through said electrically conductive substance for at least 10 minutes, and;

removing said alternating current flow through said electrically conductive substance after at least 10 minutes, and administering said substance within 7 days after removing said alternating current flow through said substance.

4. A method for preparing a substance for use as a medicament in providing treatment to the body of a recipient, said method including the steps of:

placing an electrically conductive substance in a container such that said electrically conductive substance is separated from the body area of the recipient in need of treatment;

locating at least one pair of electrodes within said container of electrically conductive substance and spacing said pair of electrodes from one another, and;

connecting an alternating current source with substantially no DC bias to said at least one pair of electrodes and operating said current source to generate an alternating current with an output power of at least approximately 10 milliwatts per milliliter of said electrically conductive substance in said container so that current flows between said electrodes and through said electrically conductive substance.

5. A method for preparing a substance for use as a medicament in providing treatment to the body of a recipient, said method including the steps of:

placing an electrically conductive substance in a container such that said electrically conductive substance is separated from the body area of the recipient in need of treatment;

locating at least one pair of electrodes within said electrically conductive substance of said container and spacing said pair of electrodes from one another;

connecting an alternating current source to said at least one pair of electrodes and operating said current source to generate alternating current having a frequency lying in a range of frequencies between about 10 KHz and about 1 MHz, and an output power of said alternating current source of at least approximately 10 milliwatts per milliliter of said electrically conductive substance in said container, so that current flows through said electrically conductive substance and between said pair of electrodes for at least about 10 minutes;

removing said alternating current flow through said electrically conductive substance, and;

administering said substance within 7 days after removing said alternating current flow through said substance.

6. A method for preparing a substance for use as a medicament in providing treatment to the body of a recipient, said method including the steps of:

placing an electrically conductive substance in a container such that said electrically conductive substance is separated from the body area of the recipient in need of treatment, and;

locating at least one pair of electrodes within said container of electrically conductive substance and spacing said pair of electrodes from one another;

connecting an alternating current source to said at least one pair of electrodes and operating said current source to generate an alternating current having a frequency lying in a range of frequencies between 10 KHz and 1 MHz and an output power sufficient to raise the temperature of the electrically conductive fluid by at least three degrees Fahrenheit, so that current flows between said electrodes and through said electrically conductive substance for at least 10 minutes.

7. A method for preparing a substance for use as a medicament in providing treatment to the body of a recipient, said method including the steps of:

placing an electrically conductive substance in a container such that said electrically conductive substance is separated from the body area of the recipient in need of treatment;

locating at least one pair of electrodes within said container of electrically conductive substance and spacing said pair of electrodes from one another, and;

connecting an alternating current source to said at least one pair of electrodes and operating said current source to generate an alternating current having a frequency lying in a range of frequencies between 10 KHz and 100 KHz and an output power sufficient to raise the temperature of the electrically conductive fluid by at least three degrees Fahrenheit, so that current flows between said electrodes and through said electrically conductive substance for at least 10 minutes.

8. A substance as prepared as in any one of claims 1–7, which is applied using an apparatus to mechanically convert said electrically active substance to a fine mist, said mist being formed of clumps of molecules of said substance in micro droplet form.

9. A substance as prepared as in any one of claims 1–7, which is applied using an apparatus to mechanically convert said electrically active substance to a fine mist, said mist being formed of clumps of molecules of said substance in micro droplet form, said mist then being inhaled by the recipient into the pulmonary tract of the recipient.

10. A substance as prepared as in any one of claims 1–7, which is applied using an apparatus to mechanically convert said electrically active substance to a fine mist, said mist being formed of clumps of molecules of said substance in micro droplet form.

11. A substance as prepared as in any one of claims 1–7, which is applied using an apparatus to mechanically convert said electrically active substance to a fine mist, said mist being formed of clumps of molecules of said substance in micro droplet form, said mist then being inhaled by the recipient into the pulmonary tract of the recipient.

12. A method for preparing a substance for use as a medicament in providing treatment to the body of a recipient, said method including the steps of:
   placing an electrically conductive substance in a container such that said electrically conductive substance is separated from the body area of the recipient in need of treatment;
   locating at least one pair of electrodes within the electrically conductive substance of said container and spacing said pair of electrodes from one another;
   connecting an alternating current source to said at least one pair of electrodes and operating said current source to generate alternating current having a frequency lying in a range of frequencies between 10 KHz and 1 MHz so that current flows through said electrically conductive substance and between said electrodes for at least 10 minutes, and;
   wherein said substance is prepared for use in a manner of administering via internal injection passing through and beyond the epidermal layers of skin, internally and into the blood containing portion of the body of the recipient.

13. A method for preparing a substance for use as a medicament in providing treatment to the body of a recipient, said method including the steps of:
   placing an electrically conductive substance in a container such that said electrically conductive substance is separated from the body area of the recipient;
   locating at least one pair of electrodes within said container of electrically conductive substance and spacing said pair of electrodes from one another;
   connecting an alternating current source to said at least one pair of electrodes and operating said current source to generate an alternating current having a frequency lying in a range of frequencies between 10 KHz and 100 KHz so that current flows between said electrodes and through said electrically conductive substance for at least 10 minutes, and;
   wherein said substance is prepared for use in a manner of administering via internal injection passing through and beyond the epidermal layers of skin, internally and into the blood containing portion of the body of the recipient.

14. A method for preparing a substance for use as a medicament in providing treatment to the body of a recipient, said method including the steps of:
   placing an electrically conductive substance in a container such that said electrically conductive substance is separated from the body area of the recipient in need of treatment;
   locating at least one pair of electrodes within said container of electrically conductive substance and spacing said pair of electrodes from one another;
   connecting an alternating current source to said at least one pair of electrodes and operating said current source to generate an alternating current with an output power of at least approximately 10 milliwatts per milliliter of said electrically conductive substance in said container so that current flows between said electrodes and through said electrically conductive substance for at least 10 minutes;
   removing said alternating current flow through said electrically conductive substance after at least 10 minutes, and administering said substance within 7 days after removing said alternating current flow through said substance, and;
   wherein said substance is prepared for use in a manner of administering via internal injection passing through and beyond the epidermal layers of skin, internally and into the blood containing portion of the body of the recipient.

15. A method for preparing a substance for use as a medicament in providing treatment to the body of a recipient, said method including the steps of:
   placing an electrically conductive substance in a container such that said electrically conductive substance is separated from the body area of the recipient in need of treatment;
   locating at least one pair of electrodes within said electrically conductive substance of said container and spacing said pair of electrodes from one another;
   connecting an alternating current source to said at least one pair of electrodes and operating said current source to generate alternating current having a frequency lying in a range of frequencies between about 10 KHz and about 1 MHz, and an output power of said alternating current source of at least approximately 10 milliwatts per milliliter of said electrically conductive substance in said container, so that current flows through said electrically conductive substance and between said pair of electrodes for at least about 10 minutes;
   removing said alternating current flow through said electrically conductive substance, and;
   administering said substance within 7 days after removing said alternating current flow through said substance;
   wherein said substance is prepared for use in a manner of administering via internal injection passing through and beyond the epidermal layers of skin, internally and into the blood containing portion of the body of the recipient.

16. A method for preparing a substance for use as a medicament in providing treatment to the body of a recipient, said method including the steps of:
   placing an electrically conductive substance in a container such that said electrically conductive substance is separated from the body area of the recipient in need of treatment;

locating at least one pair of electrodes within said container of electrically conductive substance and spacing said pair of electrodes from one another;

connecting an alternating current source to said at least one pair of electrodes and operating said current source to generate an alternating current having a frequency lying in a range of frequencies between 10 KHz and 1 MHz and an output power sufficient to raise the temperature of the electrically conductive fluid by at least three degrees Fahrenheit, so that current flows between said electrodes and through said electrically conductive substance for at least 10 minutes;

wherein said substance is prepared for use in a manner of administering via internal injection passing through and beyond the epidermal layers of skin, internally and into the blood containing portion of the body of the recipient.

17. A method for preparing a substance for use as a medicament in providing treatment to the body of a recipient, said method including the steps of:

placing an electrically conductive substance in a container such that said electrically conductive substance is separated from the body area of the recipient in need of treatment;

locating at least one pair of electrodes within said container of electrically conductive substance and spacing said pair of electrodes from one another;

connecting an alternating current source to said at least one pair of electrodes and operating said current source to generate an alternating current having a frequency lying in a range of frequencies between 10 KHz and 100 KHz and an output power sufficient to raise the temperature of the electrically conductive fluid by at least three degrees Fahrenheit, so that current flows between said electrodes and through said electrically conductive substance for at least 10 minutes;

wherein said substance is prepared for use in a manner of administering via internal injection passing through and beyond the epidermal layers of skin, internally and into the blood containing portion of the body of the recipient.

18. A substance as prepared as in any one of claims 1–7 or 12–17, wherein the substance is administered via internal injection passing through and beyond the epidermal layers of skin, and internally into the blood containing portion of the body of the recipient in a nnon-topical manner.

19. A substance as prepared as in any one of claims 1–7 or 12–17, wherein the substance is prepared for use within 7 days after removal of the alternating current flow through said substance.

20. A substance as prepared as in any one of claims 1–7 or 12–17, for use as a medicament in combination with other medicaments.

21. A substance as prepared as in any one of claims 1–7 or 12–17, for use as a treatment for any internal condition which prevents optimal blood circulation.

22. A substance as prepared as in any one of claims 1–7 or 12–17, for use in providing optimal blood circulation.

23. A substance as prepared as in any one of claims 1–7 or 12–17, for use as a treatment of any internal condition which prevents optimal heart function.

24. A substance as prepared as in any one of claims 1–7 or 12–17, for use as a medicament to improve the condition of internal connective tissue.

25. A substance as prepared as in any one of claims 1–7 or 12–17, for use as a medicament for the treatment of damaged internal protein structures.

26. The method as described as in any one of claims 1–7 or 12–17 where at least one of the following;

1) chemicals, 2) cellular material, 3) drugs, and;

4) stem cells are mixed with said electrically active substance, prior to use.

* * * * *